(12) United States Patent
Guery et al.

(10) Patent No.: US 8,553,834 B2
(45) Date of Patent: Oct. 8, 2013

(54) COMPUTED TOMOGRAPHY DETECTOR MODULE

(75) Inventors: Alain Valentin Guery, Andover, MA (US); Camille Huin, Andover, MA (US); Dipak Sengupta, Boxborough, MA (US)

(73) Assignee: Analog Devices, Inc., Norwood, MA (US)

(*) Notice: Subject to any disclaimer, the term of this patent is extended or adjusted under 35 U.S.C. 154(b) by 483 days.

(21) Appl. No.: 12/885,192

(22) Filed: Sep. 17, 2010

(65) Prior Publication Data

US 2012/0069956 A1  Mar. 22, 2012

(51) Int. Cl.
*A61B 6/03* (2006.01)

(52) U.S. Cl.
USPC .......................................................... 378/19

(58) Field of Classification Search
USPC .............. 378/4, 19, 98.8; 250/208.1, 370.09; 361/718, 717, 719
See application file for complete search history.

(56) References Cited

U.S. PATENT DOCUMENTS

| | | | |
|---|---|---|---|
| 5,357,404 A | 10/1994 | Bright et al. | |
| 6,510,195 B1 | 1/2003 | Chappo et al. | |
| 6,534,340 B1 | 3/2003 | Karpman et al. | |
| 6,661,865 B1 * | 12/2003 | Popilock | 378/19 |
| 7,358,501 B2 | 4/2008 | Danzer et al. | |
| 7,382,620 B2 | 6/2008 | Khanna et al. | |
| 7,394,659 B2 | 7/2008 | Colgan et al. | |
| 2005/0258369 A1 * | 11/2005 | Wieczorek | 250/366 |
| 2006/0165214 A1 * | 7/2006 | Mattson et al. | 378/19 |

FOREIGN PATENT DOCUMENTS

WO  WO 2009/072056 A2  6/2009

OTHER PUBLICATIONS

International Search Report and Written Opinion of the International Searching Authority in counterpart International Application No. PCT/US2011/049963, report dated Dec. 22, 2011.

* cited by examiner

*Primary Examiner* — Irakli Kiknadze
(74) *Attorney, Agent, or Firm* — Kenyon & Kenyon LLP (57) ABSTRACT

A computed tomography detector module can include a detector element, a frame, and a converter element. The detector element can be configured to detect electromagnetic radiation at a detection plane and output one or more analog detection signals. The frame can connect to the detector element and include a shield portion, parallel to the detection plane, configured to at least partially block X-rays. The converter element can include a substrate having connector and component substrate portions, the connector substrate portion thicker in a direction perpendicular to the detection plane than the component substrate portion and configured to extend through an aperture of the frame, the component substrate portion having at least one substrate surface parallel to the detection plane with one or more electrical components attached thereto. The detector module can optionally include a heat sink, which can have a top surface separated from the component substrate portion and components attached thereto by a separation gap. A computed tomography scanner can include the detector module.

26 Claims, 10 Drawing Sheets

COMPUTED TOMOGRAPHY DETECTOR MODULE

BACKGROUND INFORMATION

Figure 1:
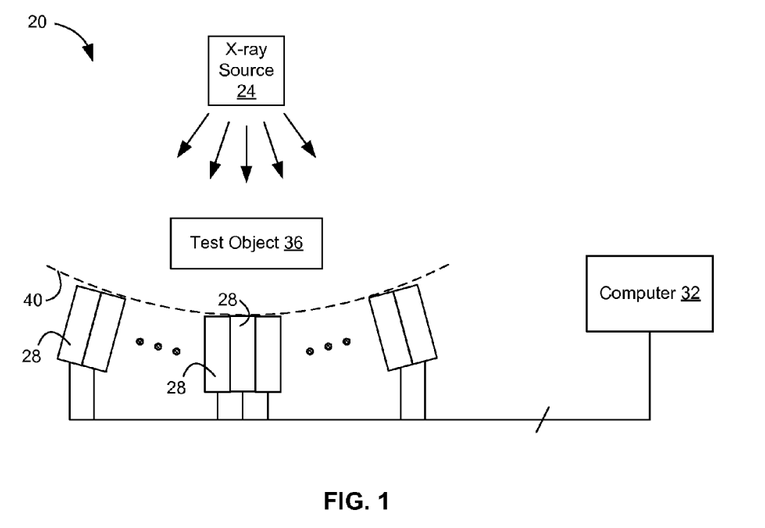
FIG. 1 depicts an embodiment of a CT scanner.

Computed tomography (CT) scanners can be used to produce two- and three-dimensional digital images of test objects. FIG. 1 depicts an exemplary embodiment of a CT scanner 20 having an X-ray source 24, a plurality of detector modules 28, and a computer 32. The X-ray source 24 produces X-rays in a direction toward a test object 36 and the detector modules 28. The detector modules 28 can convert X-rays arriving at the modules 28 into electrical detection signals, which can be transmitted, in digital or analog form, to the computer 32 for processing. The computer in turn converts the electrical detection signals into two- and three-dimensional digital images, and typically displays or sends such images to a user. The presence of the test object 36, which is to be imaged, between the X-ray source 24 and the detector modules 28 affects the transmission of the X-rays from the source 24 to the detector modules 28. The test object can typically include humans or other animals or living creatures, as well as inanimate objects, such as luggage or trucks.

Several problems exist, however, in designing and constructing CT scanners. To produce images, detector modules 28 are typically arranged adjacent to each other to provide a uniform detection capability at a curved overall detection surface 40. Thus, it is desirable to produce detector modules 28 that can be tiled next to each other. However, achieving desirable performance metrics of the detector module 28 in the operational environment of the CT scanner 20 can conflict with this desire to reduce the module size and profile. For example, achieving desirable performance metrics of analog-to-digital conversions that may take place in the module 28 can dictate the use of a plurality of analog and digital integrated circuits, each generating heat, which tends to put heat transfer constraints on module size and profile reduction. This can be exacerbated in the CT scanner operational environment because X-rays impinging on the detector modules 28 can generate further heat that may need to be transferred or distributed. The presence of X-rays in proximity and possibly coinciding with electronic circuitry, such as the analog and digital integrated circuits, also presents concerns of such radiation deleteriously affecting electrical circuitry operation. Moreover, in operation, the detection surface 40 and thus the plurality of detector modules 28 are typically rotated about the test object 36, imposing mechanical accelerations and vibrations on the detector module 28. A stable and strong detector module assembly, having a relatively light weight, can thus be further desirable.

Therefore, there is a need for a CT detector module capable of providing as large a resolution as possible to a CT scanner, the detector module having a reduced size, profile and weight, yet being of stable and strong construction, capable of sufficiently transferring heat generated by circuitry and X-rays, and capable of error-resistant electrical operation within the X-ray-proximate environment of the CT scanner.

BRIEF DESCRIPTION OF THE DRAWINGS

So that features of the present invention can be understood, a number of drawings are described below. However, the appended drawings illustrate only particular embodiments of the invention and are therefore not to be considered limiting of its scope, for the invention may encompass other equally effective embodiments.

DETAILED DESCRIPTION OF EXAMPLE EMBODIMENTS

An embodiment of the computed tomography detector module 28 can include a detector element, a frame, and a converter element. The detector element can be configured to detect electromagnetic radiation at a detection plane and output one or more analog detection signals. The frame can be configured to connect to the detector element and include a shield portion, parallel to the detection plane, to at least partially block X-rays. The converter element can include a substrate having a connector portion and a component portion, the connector portion thicker in a direction perpendicular to the detection plane than the component portion and configured to extend through an aperture of the frame, and the component portion having at least one substrate surface parallel to the detection plane with one or more electrical components attached thereto. The detector module can also include a heat sink separated from the component substrate portion and components attached thereto by a separation gap to control heat transfer and accommodate mechanical vibrations therebetween.

Figure 2:
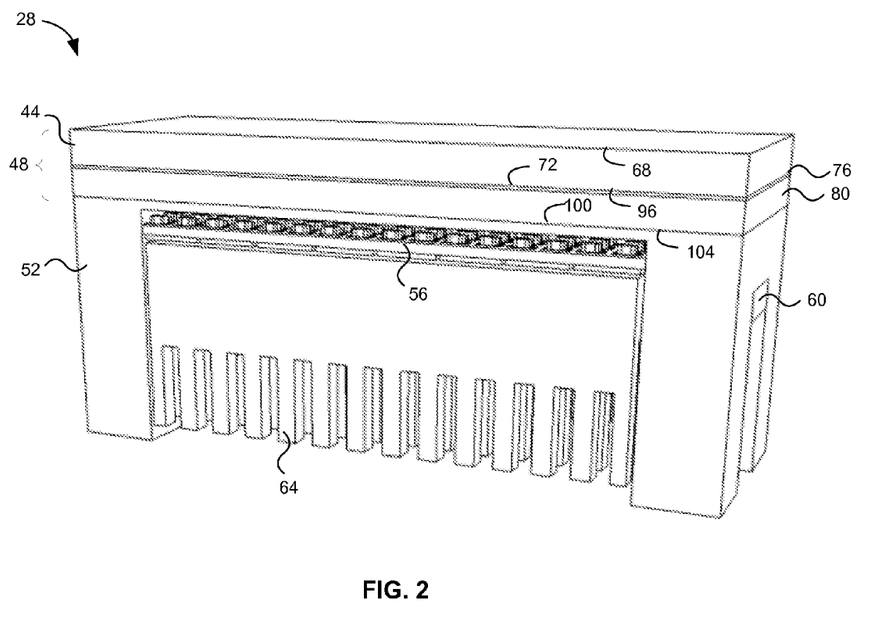
FIG. 2 depicts a perspective view of an embodiment of a CT detector module suitable for use in the CT scanner.
Figure 3:
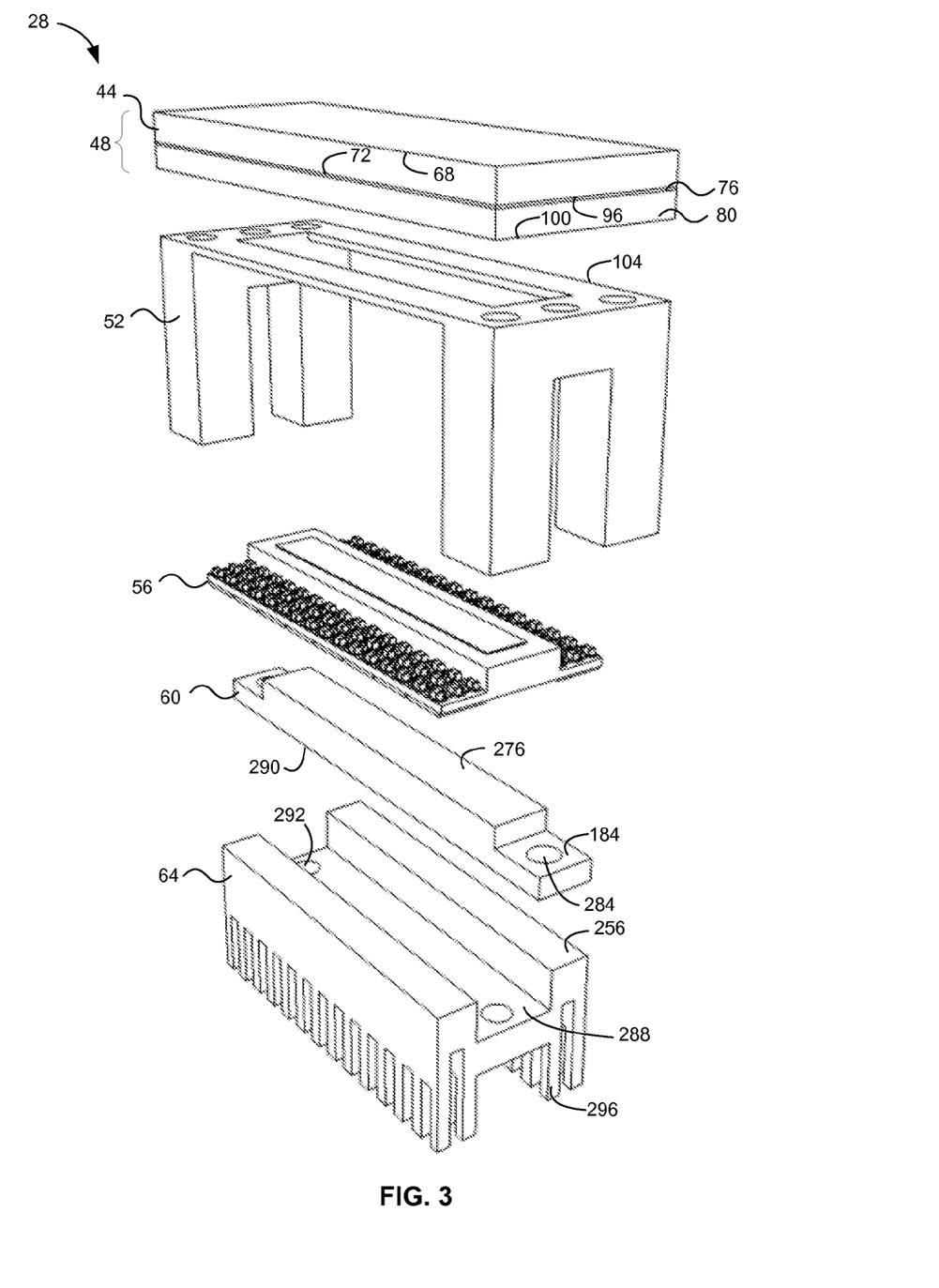
FIG. 3 depicts an exploded perspective view of the embodiment of the CT detector module depicted in FIG. 2.
Figure 4:
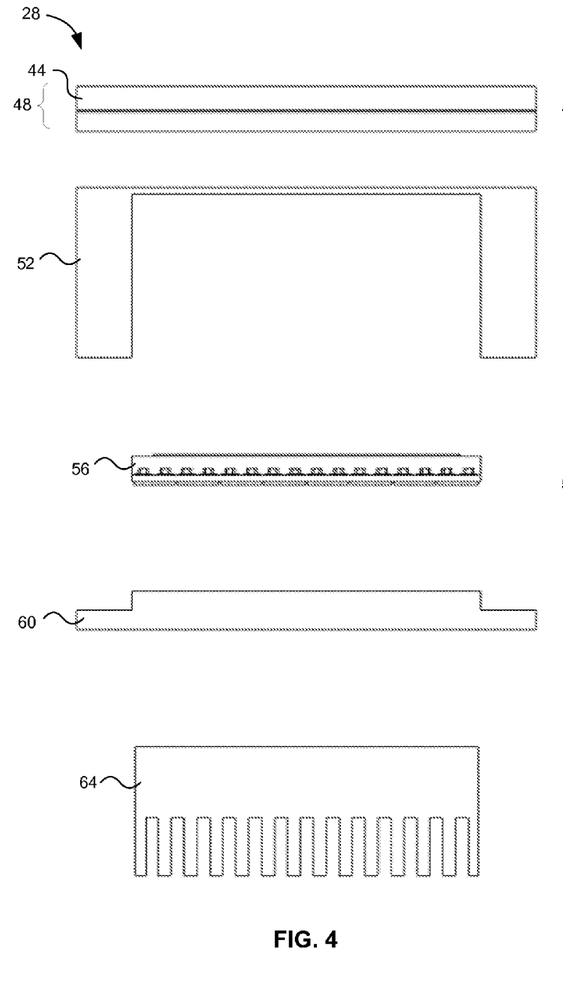
FIG. 4 depicts an exploded front view of the embodiment of the CT detector module depicted in FIG. 2.
Figure 5:
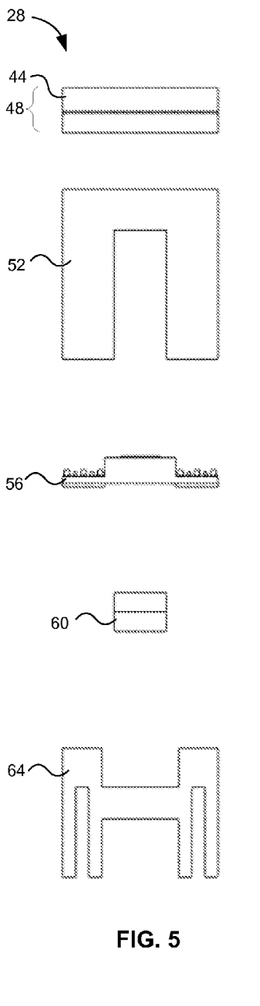
FIG. 5 depicts an exploded side view of the embodiment of the CT detector module depicted in FIG. 2.

FIG. 2 depicts a perspective view of an embodiment of the detector module 28 suitable for use in the CT scanner 20. FIG. 2 depicts the embodiment in an assembled state, as it can be employed in the CT scanner 20. FIG. 3 depicts an exploded perspective view of the embodiment of the detector module 28 of FIG. 2, affording a more detailed view of components of the embodiment of the detector module 28. FIGS. 4 and 5 depict front and side views, respectively, of the exploded embodiment of the detector module 28 depicted in FIGS. 2 and 3. The depicted embodiment of the detector module 28 includes the scintillator element 44, the detector element 48, the frame 52, the converter element 56, a bracket 60, and the heat sink 64. Other embodiments of the detector module 28 can include all or any possible subset of these components. Also, although the detector module 28 is suitable for use in the CT scanner 20, and discussion herein addresses aspects of this suitability, the detector module 28 can also be used in any apparatus utilizing an electromagnetic radiation detector. Such an apparatus can optionally utilize radiation other than X-ray radiation to image a test object, and components of embodiments of the detector module 28 can be adapted to operate accordingly.

Embodiments of the detector element 48 can include a scintillator element 44 that can be configured to receive a first type of electromagnetic radiation having a first wavelength, such as X-ray radiation, and emit a second type of electromagnetic radiation having a second wavelength, such as radiation in the light, or visible radiation, spectrum. The scintillator element 44 can optionally instead or additionally convert between other types of electromagnetic radiations. The scintillator element 44 can include top and bottom surfaces 68, 72, and have a thickness. The top surface 68 can be configured to receive the X-ray radiation, and the bottom surface 72 can be configured to emit the visible radiation. As depicted in FIGS. 2-5, the top and bottom surfaces 68, 72 can be substantially rectangular, and the scintillator can occupy a volume corresponding to a rectangular slab coinciding in cross-sectional area to a maximum cross-sectional area, i.e., detection profile, of the detector module 28. Embodiments of the scintillator element 44 can include a layer of material exhibiting luminescence upon exposure to the first type of radiation, such as a layer of one or more of an organic crystal, an organic liquid, a plastic, an inorganic crystal, a gas, or a glass exhibiting such luminescence.

Embodiments of the detector element 48 can also include a photodiode array 76 and a substrate 80. The photodiode array 76 can include a plurality of photodiodes 84 configured to receive the radiation output by the scintillator element 44 at a detection plane 88 and convert this received radiation into a plurality of analog detection signals VADetect. The detection plane 88 can be divided into a plurality of pixels 92, and the photodiode array can generate the plurality of analog detection signals VADetect such that each signal corresponds to a single pixel 92 of received radiation at the detection plane 88. Similar to embodiments of the scintillator element 44, as depicted in FIGS. 2-5 the array of photodiodes 76 and associated substrate 80 can collectively have top and bottom surfaces 96, 100 and a thickness, and occupy a volume corresponding to a rectangular slab coinciding in cross-sectional area to a maximum cross-sectional area, i.e., detection profile, of the detector module 48.

Figure 6A:
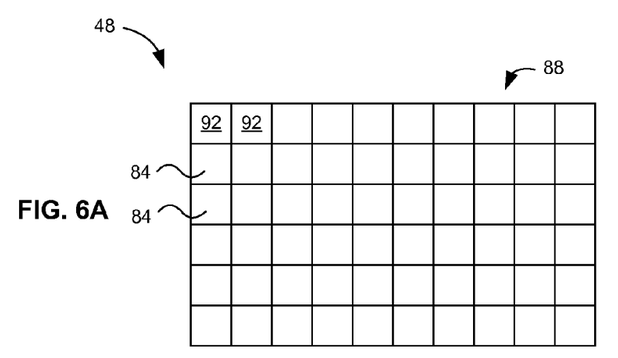
FIGS. 6A-6C depict top, front and side views, respectively, of an embodiment of an array of photodiodes and substrate of an embodiment of the detector element.
Figure 6B:
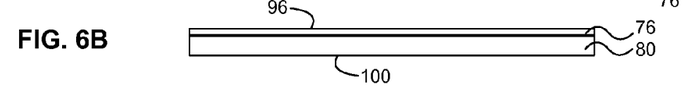
Figure 6C:
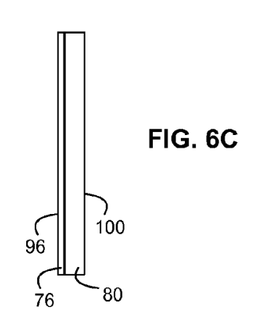

In embodiments, the detection plane 88 of the detector element 48, as discussed herein, can be considered to be the plane at which the array of photodiodes 76 is configured to be sensitive to receive the electromagnetic radiation output from the scintillator element 44 for detection and conversion to the analog detection signals VADetect. Each photodiode 84 can be considered to include a finite surface 92, i.e., pixel, upon which it is receptive to receive radiation for detection and conversion to an analog detection signal VADetect. The detection plane 88 can thus be considered to be the sum of the receptive surfaces 92 of each of the plurality of photodiodes 84 of the array of photodiodes 76. The array of photodiodes 76 can include a plurality of individual photodiodes 84 arranged in a geometrical pattern, such as a rectangular array, each photodiode 84 including its individual detection surface 92, and collectively the array of photodiodes providing the collective detection plane 88. FIGS. 6A-6C depict top, front and side views, respectively, of an embodiment of the array of photodiodes 76 and associated substrate 80. The top view of the depicted embodiment shows the individual detection surfaces 92 of each photodiode 84 and the collective formation of the overall detection plane 88 of the array of photodiodes 76 by the combination of the individual detection surfaces 92. The individual detection surfaces 92 and the collective detection plane 88 can be considered to sit at the top surface 96 of the embodiment of the array of photodiodes 76 and associated substrate 80 depicted in FIGS. 6A-6C. Other embodiments of the detector element 48, or individual detection surfaces 92 of photodiodes 84 and collective detection plane 88 of the photodiode array 76, are possible. For example, in other embodiments the geometrical shape of the individual detection surfaces 92 or collective detection plane 88 may differ from purely square or rectangular as depicted in FIGS. 6A-6C, and may include gaps, or non-detecting portions, interspersed among the individual detection surfaces 92. Also, in other embodiments, the actual active detection surfaces 92 and detection plane 88 may not be located at the top surface 96 of the array of photodiodes 76, and can instead be located underneath one or more transparent layers of the array of photodiodes 76.

As depicted in FIGS. 2-5, the substrate 80 can also occupy a volume corresponding to a rectangular slab and coincide in cross-sectional area to a maximum cross-sectional area, i.e., detection profile, of the detector module 28. A bottom surface 100 of the substrate 80 (coinciding with the bottom surface 100 of the detector element 48) can be configured to connect to a top surface 104 of the frame 52 of the detector module 28. The bottom surface 100 of the substrate 80, and detector element 48, can be parallel to the detection plane 88 of the detector element 48. The substrate 80 can be implemented in various ways. The substrate 80 and array of photodiodes 76 can optionally be integral to each other, e.g., be a single integrated circuit, with the substrate 80 being a silicon or other semiconductor substrate in and upon which the array of photodiodes 76 can be formed by a substrate processing process. The substrate 80 can alternatively be processed or formed separately from the array of photodiodes 76, and in such embodiments can include either a semiconductor or ceramic substrate 80 attached to the array of photodiodes 76.

In other embodiments of the detector element 48, the scintillator element 44 can optionally be an electronic scintillator element 44, i.e., of a type that converts directly from the first type of electromagnetic radiation, e.g., X-ray radiation, to the analog electric detection signals VADetect without producing the second type of electromagnetic radiation as an intermediate output. Embodiments of the detector element 48 including such an electronic scintillator element 44 can optionally omit the photodiode array 76, as its function can be replaced by that of the electronic scintillator element 44. In such embodiments, the electronic scintillator element 44 can be connected to, integral with, or omit the substrate 80, and the detection plane 88 of the detector element 48 can be considered to be the plane at which the electronic scintillator element 48 is configured to be sensitive to receive the first electromagnetic radiation for detection and conversion to the analog detection signals VADetect.

Figure 7A:
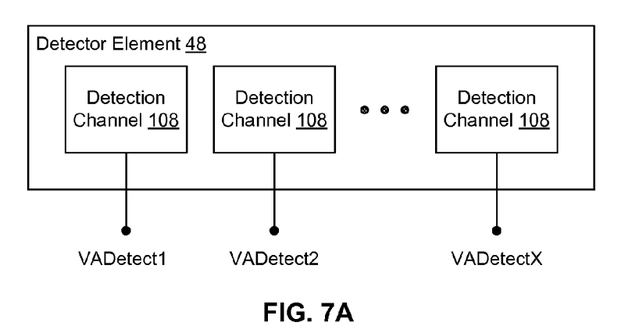
FIGS. 7A-7B are circuit schematics depicting embodiments of circuits that can be implemented by the detector element.
Figure 7B:
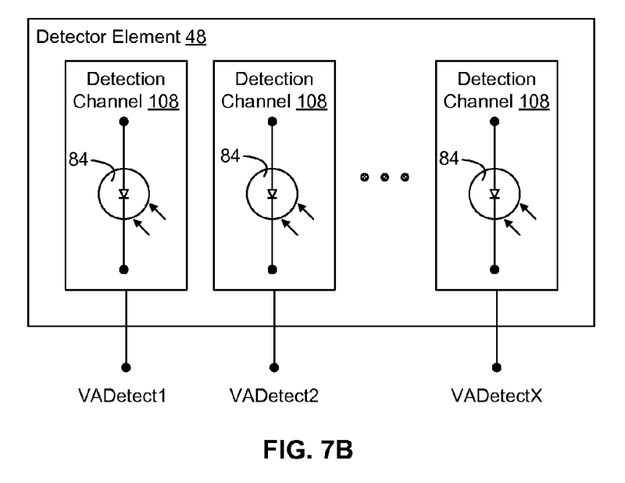

FIGS. 7A and 7B are circuit schematics depicting embodiments of circuits that can be implemented by the detector element 48. The depicted embodiments can include one or more, e.g., a plurality, of detection channels 108. Each detection channel 108 provides an analog detection signal VADetect, representing a measure of a radiation received at the detector element, e.g., the radiation received directly at the surface of the scintillator element 44, as encompassed by the embodiment of FIG. 7A, or the radiation received at the photodiode detection surfaces 92 from the scintillator element 44, as encompassed by the embodiment of FIG. 7B, in which the detection channel 108 can include at least one of the photodiodes 84 of the array of photodiodes 76 and any other associated circuitry used to provide the detection signal VADetect. The detector element 48 can be configured to produce one or more, e.g., a plurality, of the analog detection signals VADetect1, VADetect2 . . . VADetectX, representing the output of the one or more detection channels 108. The analog detection signals VADetect can represent a detectable property of the radiation received at the scintillator element 44 or the photodiode detection surfaces 92. For example, the analog detection signals VADetect can represent a detected measure of the intensity of such radiation as a function of time.

Figure 8:
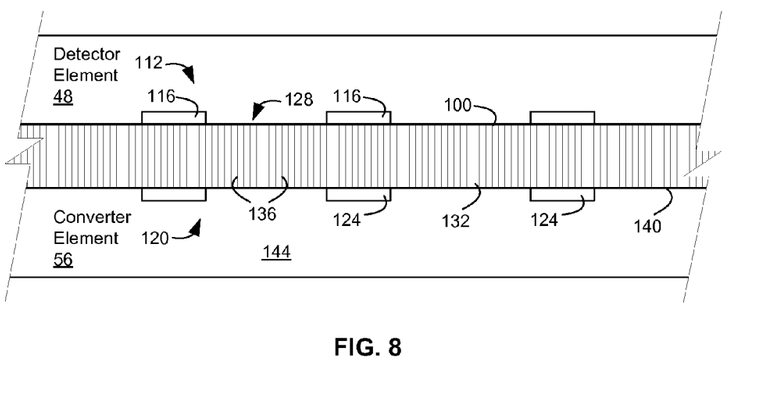
FIG. 8 depicts a partial cross-sectional view of an embodiment of an electrical interconnection of the detector element and a converter element.

The detector element 48 can include a connector 112 to provide mechanical and electrical connection to circuit leads having the plurality of analog detection signals VADetect1, VADetect2 . . . VADetectX. The connector 112 can take a variety of forms, including any combination of pin-shaped leads, male or female connector bodies, solder bumps, or other connector elements. The connector 112 can be attached to either or both of the photodiode array 76 or the substrate 80. For example, the connector 112 can include an array of metallic contacts 116, such as solder bumps or any portion of metal, positioned on the bottom surface of the substrate 80. The connector 112 of the detector element 48, as well as a connector 120 of the converter element 56 (which can take the form of any of the embodiments of the connector 112 of the detector element 48 described above), can optionally work in conjunction with a layer of anisotropic connection material 128 to provide an electrical pathway for the plurality of analog detection signals VADetect to travel from the detector element 48 to the converter element 56. The anisotropic connection material 128 can include a layer of flexible polymer material 132 having embedded therein metallic or otherwise electrically conductive material forming flexible conductive pathways 136 capable of electrically connecting components contacting opposite sides of such anisotropic connection material 128. FIG. 8 depicts a partial cross-sectional view of an embodiment of an electrical connection of the detector element 48 to the converter element 56, showing the anisotropic connection material 128 located between a bottom surface 100 of the detector element 48, having a first set of electrical contacts 116, and a top surface 140 of a connector substrate portion 144 of the converter element 56, having a second set of electrical contacts 124, to provide an electrical pathway for the plurality of analog detection signals VADetect to travel from the detector element 48 to the converter element 56.

Figure 9A:
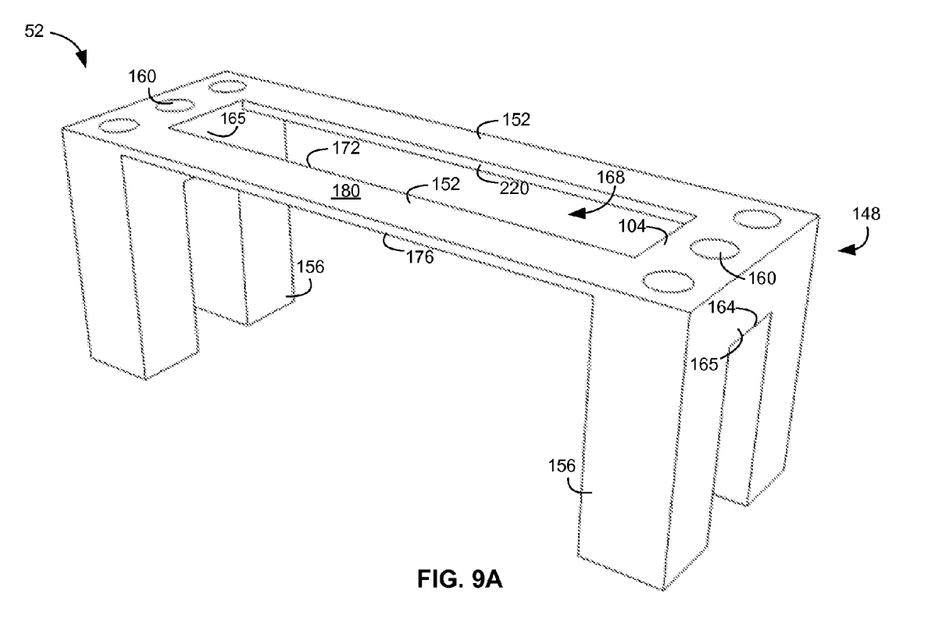
FIGS. 9A-9B depict perspective views of embodiments of a frame.
Figure 9B:
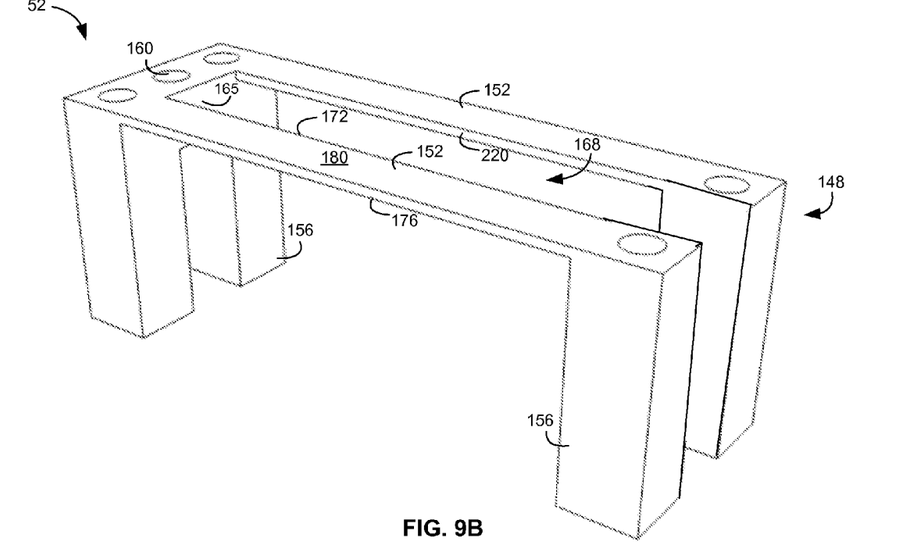
Figure 10:
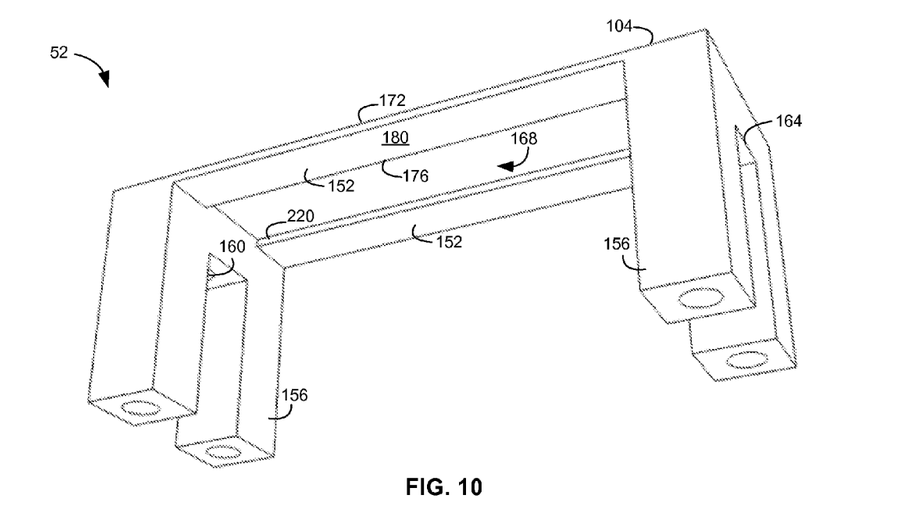
FIG. 10 depicts another perspective view of the embodiment of the frame depicted in FIG. 9A.

The detector module 28 can also include a frame 52. FIGS. 9A-9B and FIG. 10 depict perspective views, from different angles, of an embodiment of the frame 52. The frame 52 can include a top portion 148, having a top surface 104 and one or more shield portions 152, and one or more legs 156 extending away from the top portion 148. The top surface 104 can be configured to connect to a bottom surface 100 of the detector element 48, such as the bottom surface 100 of the substrate 80 of the detector element 48. Connection of the top surface 104 of the frame 52 to the bottom surface 100 of the detector element 48 can take a variety of forms, including a relatively permanent connection such as, e.g., via an adhesive, or a detachable connection such as, e.g., using a mechanical connector such as a screw, clip or other detachable mechanical connector. As depicted in FIGS. 9A-9B and FIG. 10, the top portion 148 can include a receptacle 160 extending through a thickness at one location of the frame 52, from the top surface 104 to a bottom surface 164 of the top portion 148, and configured to accept a mechanical connector (not shown) connecting the bracket 60 to the frame 52. The top surface 104 of the frame 52 can include an aperture 168 extending through the top surface 104 to allow access for the connector 120 of the converter element 56 to connect to the connector 112 of the detector element 48. The aperture 168 can be sized to have an area at least as large as an area of an array of interconnections between the connector 112 of the detector element 48 and the connector 120 of the converter element 56. The top surface 104 of the frame 56 can be parallel to the detection plane 88 of the array of photodiodes 76.

The top portion 148 can also include one or more shield portions 152. The embodiment depicted in FIGS. 9A-9B and FIG. 10 includes first and second shield portions 152. The shield portions 152 can include top and bottom surfaces 172, 176, a thickness, and a cross-sectional area 180 that serves to shield a three dimensional area below the shield portions 152 that is the projection of the cross-sectional 180 area away from the detection element 48 in a direction perpendicular to the detection plane 88 of the array of photodiodes 76. The top surface 172 of the shield portion 152 can provide a portion of the top surface 104 of the frame 52, and thus be configured to connect to the bottom surface 100 of the detector element 48. The bottom surface 176 of the shield portion 152, and the thickness of the shield portion 152, can be configured to position the bottom surface 176 above and spaced apart by a separation gap from circuit components, e.g., an array of capacitors, that can optionally be connected to a component substrate portion of the converter element. The top and bottom surfaces 172, 176 of the shield portions 152 can be parallel to the detection plane 88 of the detection element 48, and the thickness of the shield portions 152, considered in the direction travelling perpendicularly from the top to bottom surface 172, 176, can be perpendicular to the detection plane 88. The shield portions 152 are configured to shield circuitry, e.g., including one or more capacitors, one or more ADC integrated circuits, or other circuit elements, that can be connected to component substrate portions of the converter element, from X-ray radiation that may be travelling from the X-ray source 24 to the detector module 28 in the CT scanner 20. To this end, the shield portions 152 can have a cross-sectional area 180, parallel to the plane of detection 88 of the array of photodiodes 76, having a shape and size configured to be at least as great as, and encompass, an area occupied by the circuit components (e.g., capacitors, ADC integrated circuits, etc.) when considering a projection of the cross-sectional area 180 of the shield portions 152 along a direction perpendicular to the detection plane 88 away from to the detection plane 88 and photodiode array 76. That is, the shield portions 152 can completely cover the capacitors, ADCs and other circuit components that can be connected to the converter element 56 when viewed from the detector-element side of the shield portions 152 along a direction perpendicular to the detection plane 88. The shield portions 152, the entire frame 52, or both, can be constructed from a material configured to at least partially prevent (by any of blocking, reflecting, absorbing, attenuating, etc.) X-rays arriving at the top surface 172 of the shield portions 152 from other areas of the CT scanner 20 (such as X-rays originating at the X-ray source 24 of the CT scanner 20) from being emitted from the bottom surface 176 of the shield portions 152 toward the circuit components attached to the converter element 56. In one embodiment, the X-ray-shielding material can be configured to prevent at least 90% of X-rays arriving at the top surface 172 of the shield portions 152 from being emitted from the bottom surface 176 of the shield portions 152. In one embodiment, the X-ray-shielding material can include copper tungsten.

The frame 52 of the detector module 28 can also include one or more legs 156 extending away from the top portion 148 of the frame 52 and the detector element 48. In the embodiment of FIGS. 9A-9B and 10, a plurality of legs 156 extend away from the top surface 104 of the frame 52 and the detector element 48 in direction perpendicular to the top surface 104 and the detection plane 88. Additionally, in the embodiment of FIG. 9A and FIG. 10, the legs 156 can each be positioned at a corner of a substantially rectangular cross-sectional perimeter of the frame 52 in a plane parallel to the detection plane 88. The spacing of the plurality of legs 156, relative to each other, can be configured to allow entry therebetween of a tab 184 of the bracket 60 of the detector module 28. The frame 52 can also optionally be configured to have a different number of legs 156. Additionally, the frame 52 can optionally be configured to selectively omit non-shield connecting portions 165 connecting legs 156. For example, as depicted in FIG. 9B, a non-shield connecting portion 165 of the frame 52 connecting the closer spaced legs 156 can be optionally omitted, resulting in a U-shaped frame cross-sectional perimeter. Other embodiments of the frame 52 are also possible.

Figure 11A:
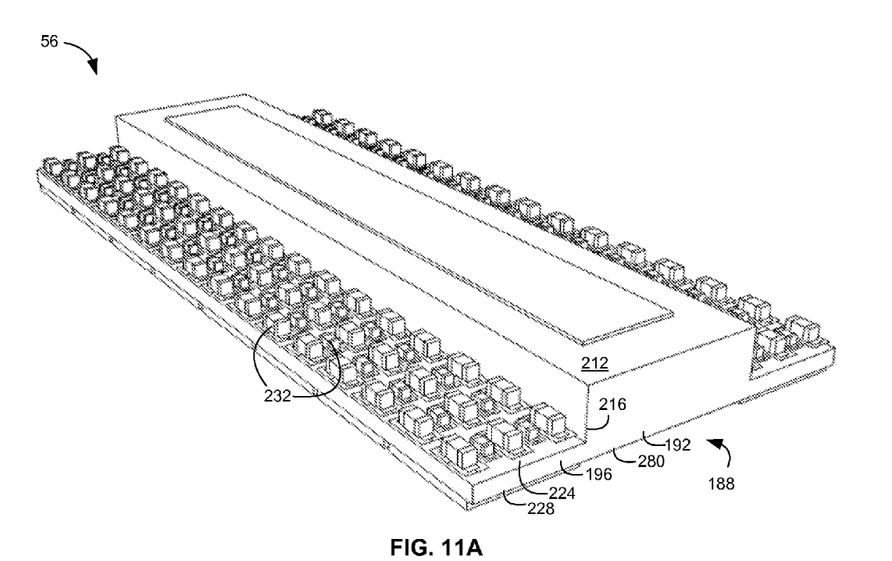
FIGS. 11A-11B depict perspective views of embodiments of the converter element.
Figure 11B:
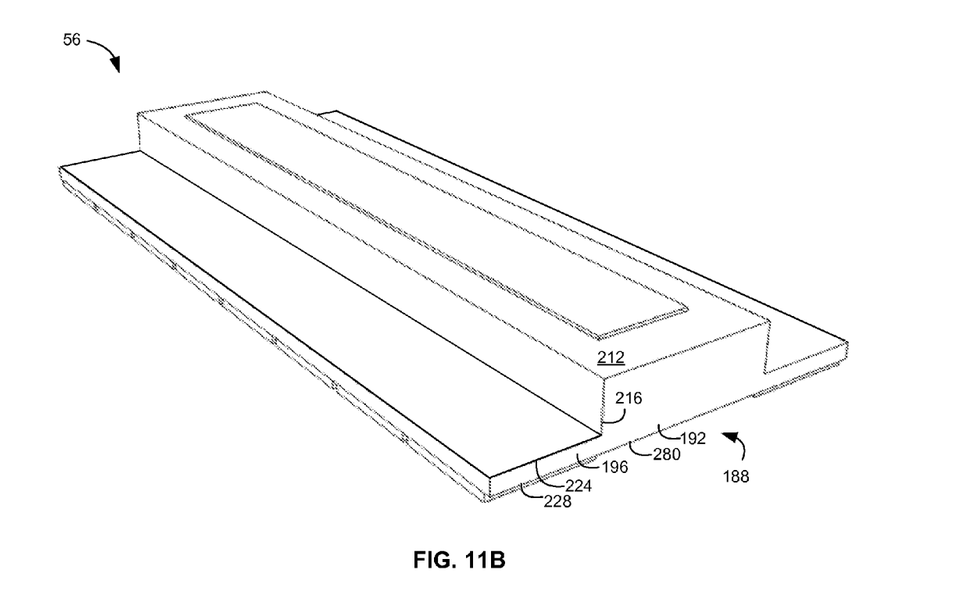
Figure 12:
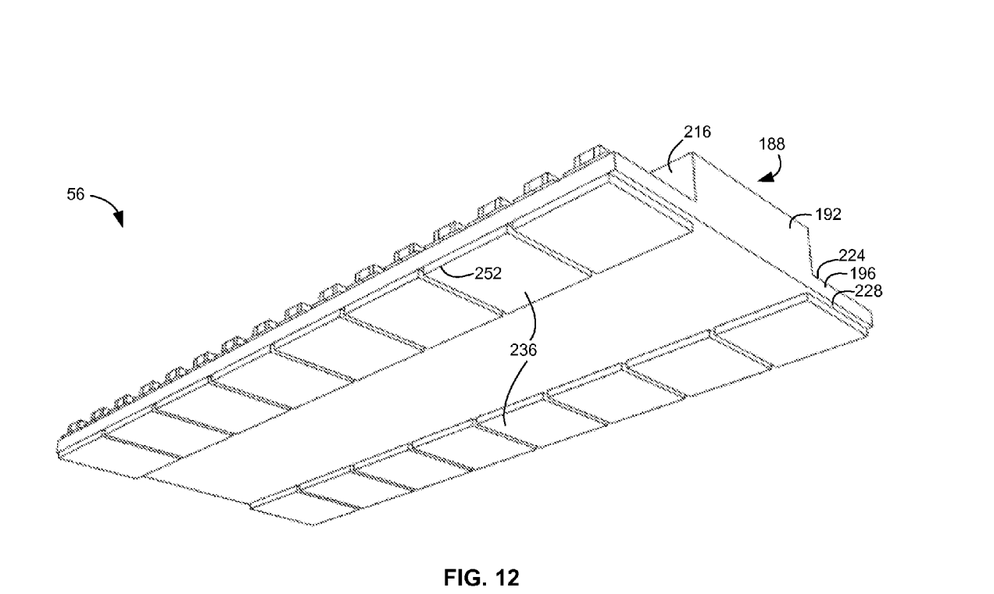
FIG. 12 depicts another perspective view of the embodiment of the converter element depicted in FIG. 11A.

The detector module 28 can also include the converter element 56. FIGS. 11A-11B and FIG. 12 depict perspective views, from different angles, of embodiments of the converter element 56. The converter element 56 can be configured to include a substrate 188 having a connector portion 192 and at least one component portion 196. In FIGS. 11A-11B and FIG. 12, the converter element substrate 188 includes two outer component portions 196, one on each side of a central connector portion 192. However, other embodiments are possible, including, e.g., a single or a plurality of connector substrate portions 192 arranged variously, e.g., in outer or central configurations relative to a component substrate portion 196; and a single or a plurality of component substrate portions 196 arranged variously, e.g., in outer or central positions relative to a connector substrate portion 192.

Figure 13A:
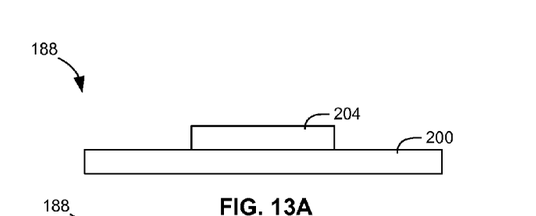
FIGS. 13A-13B depict side cross-sectional views of embodiments of a substrate.
Figure 13B:
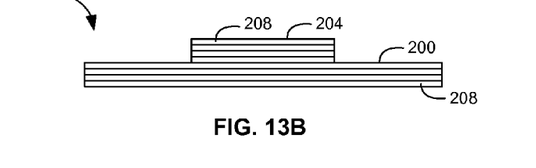

The connector substrate portion 192 can have a first thickness, as measured perpendicularly to the detection plane 88 of the detection element 48, that is greater than a second thickness of the component substrate portions 196, as also measured perpendicularly to the detection plane 88. FIGS. 13A-13B depict embodiments of the converter element substrate 188. As shown in FIG. 13A, the component substrate portions 196 can include a first substrate element 200 and the connector substrate portion 192 can include the first substrate element 200 and a second substrate element 204 stacked on top of the first substrate element 200. The first and second substrates elements 200, 204 can be formed in a variety of ways, and can include mono-layer or poly-layer substrate elements. FIG. 13B depicts an embodiment in which the first and second substrate elements 200, 204 each include a plurality of layers 208. The layers 208 can include metal, polymer, ceramic and other layers. Although a particular number of layers 208 are shown in FIG. 13B, other embodiments of the substrate elements 200, 204 can each include any total number of layers 208, from one layer 208 to a high number of layers 208. The first and second substrate elements 200, 204 can each include, e.g., printed circuit boards (PCBs), ceramic tiles, or both.

Returning to FIGS. 11A-11B and FIG. 12, as well as FIGS. 2-5, the connector substrate portion 192 of the converter element 56 can have a cross-sectional area 212 configured to fit within the aperture 168 through the top surface 104 of the frame 52. That is, the connector substrate portion 192 can optionally have a cross-sectional area 212 configured to be smaller than the area of the aperture 168. In such embodiments, a top portion of the connector substrate portion 192 can extend at least partially into or through the aperture 168 of the frame 52. Sidewalls 216 of the connector substrate portion 192 can be configured to be spaced apart from sidewalls 220 of the shield portions 152 in embodiments in which a top portion of the connector substrate portion 192 of the converter element 56 extends into the aperture 168 of the frame 52. In other embodiments, a top portion of the connector substrate portion 192 can instead sit completely below a plane of the bottom surfaces 176 of the shield portions 152. In such embodiments, the connector substrate portion 192 can have a cross-sectional area 212 either smaller or larger than the area of the aperture 168.

The component substrate portion or portions 196 of the converter element 56 can include top and bottom substrate surfaces 224, 228 occupying planes parallel to the detection plane 88 of the detector element 48. As depicted in FIGS. 11A-11B and FIG. 12, the top substrate surfaces 224 face the detector element 48 and the bottom substrate surfaces 228 face away from the detector element 48. The component substrate portions 196 can also be configured to receive one or more circuit components attached thereto. As variously depicted in the embodiment of FIGS. 11A-11B and FIG. 12, the attached circuit components can include one or more, e.g., a plurality, of capacitors 232, e.g., discrete capacitors, and one or more, e.g., a plurality of ADC integrated circuits 236. In other embodiments, the one or more circuit components can include other types of circuit components. A plurality of discrete capacitors 232 can be arranged in two dimensional arrays attached to the top surface 224 of the component substrate portion 196, and a plurality of ADC integrated circuits 236 can be arranged adjacent to each other in rows and attached to the bottom substrate surface 228 of the component substrate portion 196. Other arrangements of the capacitors 232 and ADC integrated circuits 236 on the top and bottom surfaces 224, 228 are also possible. For example, although the arrangement of the capacitors 232 on the top substrate surface 224 and the ADC integrated circuits 236 on the bottom substrate surface 228 can have specific benefits, as discussed below, other arrangements, e.g., including the capacitors 232, ADC integrated circuits 236, or other circuit components arranged variously on either or both of the top and bottom substrate surfaces 224, 228, can have other benefits. For example, as depicted in FIG. 11B, the top surface 224 of the component substrate portion 196 can optionally have no components attached thereto. In other embodiments, the top surface 224 of the component substrate portion 196 can be configured to have one or more components in addition to or other than capacitors 232 attached thereto, and the bottom surface 228 of the component substrate portion 196 can be configured to have one or more components in addition to or other than ADC integrated circuits 236 attached thereto.

Figure 14A:
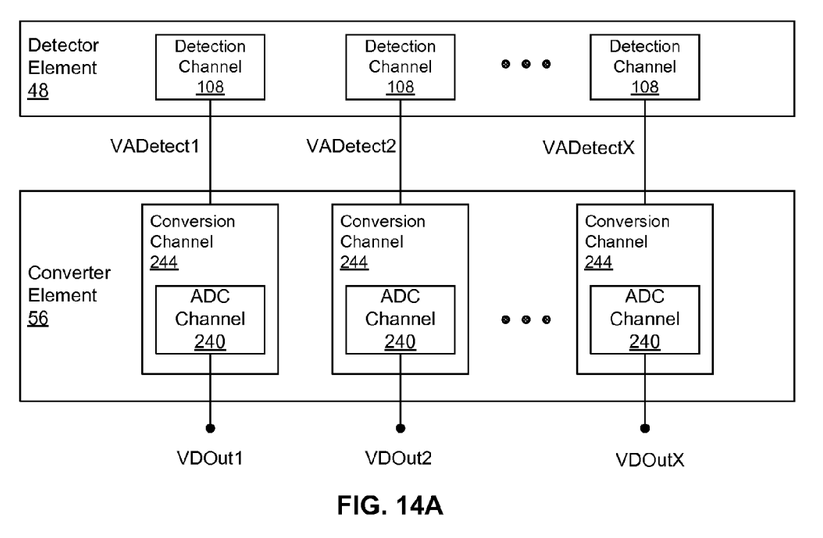
FIGS. 14A-14B are circuit schematics depicting embodiments of circuits that can be implemented by the detector element and the converter element.
Figure 14B:
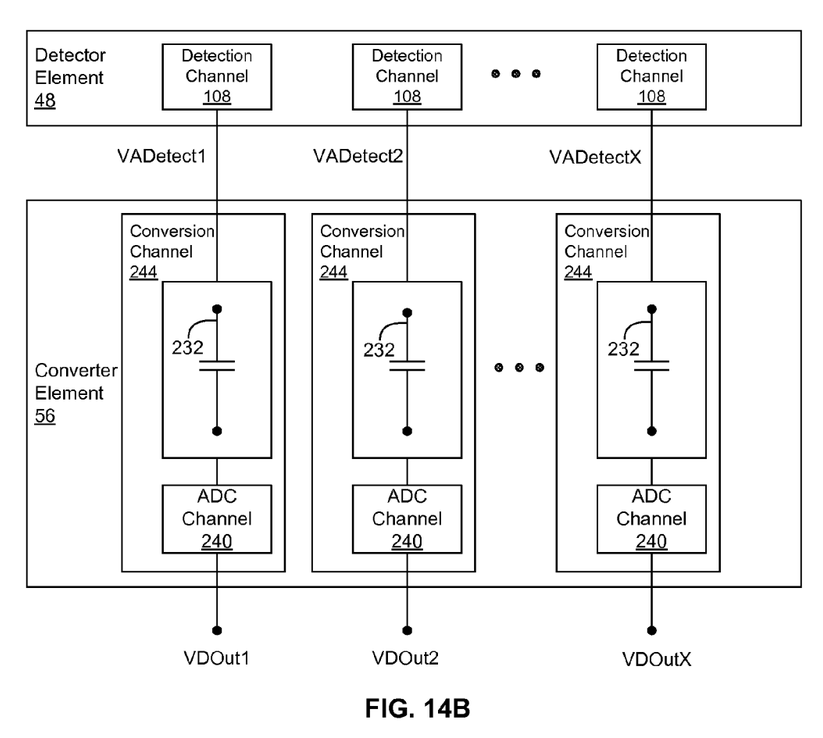

The components attached to the substrate 188 of the converter element 56 can optionally include at least one ADC channel 240 of the ADC integrated circuits 236 for each detection channel 108 of the detector element 48. FIGS. 14A and 14B are circuit schematics depicting embodiments of circuits that can be implemented by the detector and converter elements 48, 56. The detector element 48 can include one or more, e.g., a plurality, of detection channels 108 and the converter element 56 can include one or more, e.g., a plurality, of conversion channels 244. In the embodiment of FIG. 14A, the conversion channels 244 can each include at least one ADC channel 240. Optionally, as depicted in the embodiment of FIG. 14B, the conversion channels 244 can each include at least one capacitor 232 and at least one ADC channel 240. The capacitors 232 of the conversion channels 244 can be arranged in various ways. For example, the capacitor 232 can have one terminal connected to the analog detection output signal VADetect generated by the detection channel 108 and another terminal connected either to ground or a power supply. In such an embodiment, the capacitor 232 can act as a balancing load on a signal transmission path, and can be used for, e.g., filtering and compensation purposes. The capacitor 232 can alternatively have one terminal connected to the analog detection signal VADetect generated by the detection channel 108 and another terminal connected to an input of the ADC channel 240 of the conversion channel 244. The ADC channel 240 can be configured to receive at least one analog detection signal VADetect, or an analog signal derived from the analog detection signal VADetect, from a detection channel 108 and convert the analog detection signal VADetect to a digital output signal VDOut that is a digital representation of the analog detection signal VADetect. Each of the one or more ADC integrated circuits 236 can include at least one ADC channel 240 and optionally include a plurality of the ADC channels 240. For example, each ADC integrated circuit 236 can be a multi-channel ADC integrated circuit 236 having a plurality of ADC channels 240.

Figure 15:
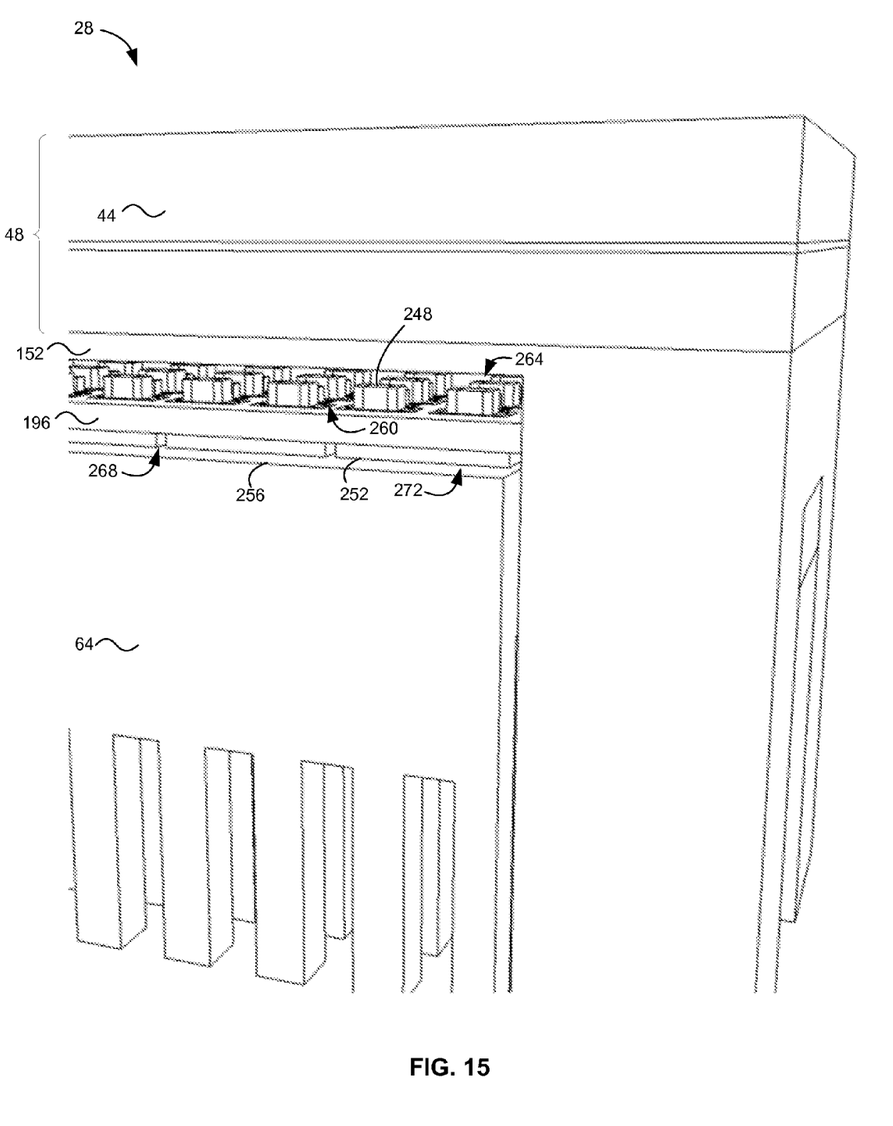
FIG. 15 is a detail perspective view of a portion of the embodiment of the detector module depicted in FIG. 2.

The converter element 56 can be configured within the detector module 28 so that the top and bottom substrate surfaces 224, 228 of the component substrate portions 196, as well as external surfaces of the one or more circuit components, e.g., capacitors 232 and ADC integrated circuits 236 in embodiments having such components attached thereto, are spaced apart from the bottom surface 176 of the shield portions 152 of the frame 52 and a top surface 256 of the heat sink 64 by separation gaps. FIG. 15 depicts a partial perspective view of an embodiment of the detector module 28, showing closer detail of a positioning of portions of the converter element 56 relative to the detector element 48 and the heat sink 64. In the depicted embodiment, a first separation gap 260 separates the top substrate surface 224 of the component substrate portion 196 of the converter element 56 from the bottom surface 176 of the shield portion 152 of the frame 52. A second separation gap 264 separates a top external surface 248 of the plurality of capacitors 232, or other circuit components attached to the top substrate surface 224 of the component substrate portion 196, from the bottom surface 176 of the shield portion 152. Similarly, in the depicted embodiment, a third separation gap 268 separates the bottom substrate surface 228 of the component substrate portion 196 of the converter element 56 from a top surface 256 of the heat sink 64, and a fourth separation gap 272 separates a bottom external surface 252 of the plurality of ADC integrated circuits 236 from the top surface 256 of the heat sink 64. The plurality of capacitors 232 typically do not generate much heat, thus a radiative and convective heat transfer mechanism from the capacitors 232 can be sufficient and the first and second separation gaps 260, 264 between the top substrate surfaces 224 of the component substrate portions 196 and the top surfaces 248 of the capacitors 232 and the bottom surface 176 of the shield portions 152 can optionally be maintained free of any material other than air or some other gaseous material. The ADC integrated circuits 236, by contrast, can typically generate appreciable heat, and thus a conductive heat transfer mechanism from the ADC integrated circuits 236 can be desirable, and thus optionally the separation gap 272 between the bottom external surfaces 252 of the ADC integrated circuits 236 and the top surface 256 of the heat sink 64 can be filled with a thermally conductive material, such as a thermal gel, paste, glue or pad, having at least greater than a predetermined thermal conductivity. The presence of the thermally conductive material can provide an efficient heat transfer path between the plurality of ADC integrated circuits 236 and the heat sink 64. The malleable or elastic nature of a gel, paste, glue or pad also allows the separation gaps 272 between solid components such as the ADC integrated circuits 236 and the heat sink 64 to be maintained, which can be desirable to provide a mechanical tolerance in the assembly of the detector module 28 to accommodate for possible vibrations during operation of the CT scanner 20. The thermally conductive material can optionally be configured to have a thermal conductivity value at least greater than about 30 W/(m·K). In addition to or instead of the above exemplary option thermal conductivity values, the thermally conductive material can optionally be configured to allow no greater than about a 15° C. temperature difference between the top surface 256 of the heat sink 64 and the external surfaces 252 of the ADC integrated circuits 236.

Returning to FIGS. 2-5, the detector module 28 can be configured to include the bracket 60 and the heat sink 64. As depicted in FIGS. 2-5, the bracket 60 can include a top surface 276 configured to connect to a bottom surface 280 of the connector substrate portion 192 of the converter element 56. The connection of the top surface 276 of the bracket 60 to the bottom surface 280 of the connector substrate portion 192 can either be a direct connection or an indirect connection having a gel or paste therebetween. The bracket 60 can also include a plurality of receptacles 284 configured to receive a mechanical connector element (not shown), such as a screw or clip, to mechanically fasten together elements of the detector module 28, such as the frame 52, bracket 60, and heat sink 64, which can all include similar receptacles.

As depicted in FIGS. 3-5, the heat sink 64 can include first top surfaces 256, a second top surface 288, one or more receptacles 292 and one or more fins 296. The first top surfaces 256 can be configured to be proximate to, but separated from by separation gaps 272, 268, the bottom external surfaces 252 of the plurality of ADC integrated circuits 236 and the bottom substrate surfaces 228 of the component substrate portions 196 of the converter element 56. The second top surface 288 can be configured to mate to a bottom surface 290 of the bracket 60. The one or more receptacles 292 can be configured to receive mechanical connectors to mechanically fasten together elements of the detector module 28, such as the frame 52, bracket 60, and heat sink 64. The one or more fins 296 can be sized and spaced apart from each other in a two dimensional array to enable efficient radiation and convection away from the heat sink 64 of heat transferred out of the plurality of ADC integrated circuits 236. As depicted, a plurality of the fins 296 can include a volume formed by a square or rectangular cross-section projected away from the detector element 48 in a direction perpendicular to the detection plane 88.

Additional embodiments of the detector module 28 are possible. For example, any feature of any of the embodiments of the detector module 28 described herein can optionally be used in any other embodiment of the detector module 28. Also, embodiments of the detector module 28 can include any subset of the components or features described herein. An embodiment of a CT scanner 20 can include any embodiment of the detector module 28.

What is claimed is:
1. A computed tomography detector module, comprising:
  a detector element configured to detect electromagnetic radiation arriving at a detection plane;
  a frame including a shield portion to at least partially block X-rays travelling perpendicular to the detection plane, the shield portion connected to a bottom surface of the detector element and positioned between the detector element and a component substrate portion of a converter element;

the converter element including a connector substrate portion and the component substrate portion, the connector substrate portion extending through an aperture in the shield portion of the frame and having a greater thickness perpendicular to the detection plane than the component substrate portion; and one or more circuit components attached to at least one surface of the component substrate portion.

2. The computed tomography detector module of claim 1, wherein the shield portion includes a cross-sectional area having a projection, perpendicular to the detection plane, that covers the one or more circuit components.

3. The computed tomography detector module of claim 1, wherein the one or more circuit components include one or more analog-to-digital converter (ADC) integrated circuits.

4. The computed tomography detector module of claim 1, wherein the at least one surface of the component substrate portion is parallel to the detection plane, and includes at least one of: a top surface of the component substrate portion or a bottom surface of the component substrate portion.

5. The computed tomography detector module of claim 1, wherein the detector element includes a photodiode array.

6. The computed tomography detector module of claim 1, wherein the detector element detects electromagnetic radiation at a plurality of pixels of the detection plane and outputs a plurality of analog detection signals that each represent a detected electromagnetic radiation at a single pixel, the one or more circuit components includes at least one analog-to-digital conversion channel for each pixel to convert the analog detection signal corresponding to that pixel to a digital detection signal.

7. The computed tomography detector module of claim 1, wherein the converter element is electrically connected to the detector element to receive one or more analog detection signals.

8. The computed tomography detector module of claim 1, wherein the one or more circuit components include at least a portion of the circuit components attached to a top surface of the component substrate portion of the converter element, and the top substrate surface and exterior surfaces of the portion of the circuit components are spaced apart from bottom surfaces of the shield portion of the frame by separation gaps.

9. The computed tomography detector module of claim 1, wherein a sidewall of the connector substrate portion of the converter element is spaced apart from side surfaces of the first and second shield portions of the frame by a separation gap.

10. The computed tomography detector module of claim 1, further comprising a heat sink having top surfaces separated from the bottom surface of the component substrate portion, wherein the one or more circuit components includes one or more analog-to-digital (ADC) integrated circuits attached to the bottom surface of the component substrate portion of the converter element, and the heat sink includes a top surface spaced apart from the bottom substrate surface and external surfaces of the one or more ADC integrated circuits by separation gaps.

11. The computed tomography detector module of claim 10, further comprising a thermally conductive material filling the separation gaps between the top surface of the heat sink and the external surfaces of the ADC integrated circuits, wherein the thermally conductive material has an elastic filling property, and includes at least one of: a gel, a paste, a glue, or a pad.

12. The computed tomography detector module of claim 11, wherein at least one of:

the thermally conductive material has a thermal conductivity having a value at least greater than about 30 W/(m·K), or the thermally conductive material is configured to allow no greater than about a 15° C. temperature difference between the top surface of the heat sink and the external surfaces of the ADC integrated circuits.

13. The computed tomography detector module of claim 1, wherein the substrate of the converter element includes a plurality of stacked layers, each occupying planes parallel to the detection plane, the connector substrate portion including a greater number of stacked layers than the component substrate portions.

14. A computed tomography scanner, comprising the computed tomography detector module of claim 1.

15. A computed tomography detector module, comprising:

a scintillator element configured to receive X-rays, convert the received X-rays to electromagnetic radiation having a different wavelength than the received X-rays, and output the electromagnetic radiation;

a detector element including a photodiode array configured to detect the electromagnetic radiation arriving at a detection plane and output a plurality of analog detection signals representing a measure of the detected radiation, a bottom surface parallel to the detection plane, and a connector configured to provide an electrical connection to the plurality of analog detection signals;

a frame, including a top surface parallel to the detection plane and connected to the bottom surface of the detector element and having an aperture extending therethrough, first and second shield portions having a cross-sectional area parallel to the detection plane and configured to at least partially block X-rays, and a plurality of legs extending away from the top surface and the detector element in a direction perpendicular to the detection plane;

a converter element including a substrate having a central connector portion and a plurality of outer component portions, the central connector portion having a thickness perpendicular to the detection plane that is greater than a thickness of the outer component portions perpendicular to the detection plane, the outer component portions having substrate surfaces occupying planes parallel to the detection plane of the detector element and having a plurality of components including a plurality of analog-to-digital converter (ADC) integrated circuits attached thereto, the central connector portion configured to extend through the aperture of the top surface of the frame; and a heat sink having surfaces positioned in proximity to but not contacting substrate surfaces of and components attached to the converter element.

16. The computed tomography detector module of claim 15, wherein the plurality of ADC integrated circuits are connected to bottom substrate surfaces of the component substrate portions.

17. The computed tomography detector module of claim 15, wherein the detector element detects the electromagnetic radiation at a plurality of pixels of the detection plane, the plurality of analog detection signals output by the detector element each represent the detected electromagnetic radiation at a single pixel, and the plurality of ADC integrated circuits are arranged in an array and include at least one conversion channel for each pixel to convert the electrical output signal corresponding to that pixel to a digital detection signal.

18. The computed tomography detector module of claim 15, wherein the converter element includes a connector connected to a top of the connector substrate portion and configured to connect to the connector of the detector element to electrically connect the plurality of analog detection signals output by the detector element to the plurality of components attached to the component substrate portions of the converter element.

19. The computed tomography detector module of claim 15, wherein the cross-sectional area of the first and second shield portions of the frame have a projection, perpendicular to the detection plane, that covers an area of the substrate surfaces of the component substrate portions of the converter element occupied by the plurality of components attached thereto, and the first and second shield portions are configured to at least partially protect the electrical operation of the plurality of components from effects of X-ray radiation.

20. The computed tomography detector module of claim 15, wherein the top substrate surfaces of the component substrate portions of the converter element are separated from bottom surfaces of the first and second shield portions of the frame by a first separation gap and exterior surfaces of the plurality of components attached to the top substrate surfaces of the component substrate portions of the converter element are separated from the bottom surfaces of the first and second shield portions of the frame by a second separation gap.

21. The computed tomography detector module of claim 15, wherein a sidewall of the connector substrate portion of the converter element is spaced apart from side surfaces of the first and second shield portions of the frame by a third separation gap.

22. The computed tomography detector module of claim 15, wherein the heat sink includes first and second top surfaces configured to be separated from the plurality components attached to a bottom substrate surface of the component substrate portions of the converter element by a fourth separation gap, and further comprising a thermally conductive material filling the separation gap between the first and second top surfaces of the heat sink and the external surfaces of the components attached to the bottom surfaces of the component substrate portions of the converter element.

23. A computed tomography detector module, comprising:
a detector element configured to detect electromagnetic radiation arriving at a detection plane;
a frame including a shield portion to at least partially block X-rays, the shield portion connected to a bottom surface of the detector element and positioned between the detector element and a component portion of a converter element;
the converter element including a connector portion and the component portion, the connector portion extending through an aperture in the shield portion of the frame; and
one or more circuit components attached to the component portion of the converter element.

24. The computed tomography detector module of claim 23, wherein the one or more circuit components include a plurality of circuit components attached to opposite-facing top and bottom substrate surfaces of the component portion of the converter element.

25. The computed tomography detector module of claim 23, further comprising a heat sink having a heat receiving surface spaced apart at a predetermined distance from a surface of the one or more circuit components.

26. The computed tomography detector module of claim 23, wherein the frame includes a plurality of legs extending away from the shield portion in a direction perpendicular to the detection plane.

* * * * *